US00PP16398P3

(12) United States Plant Patent
Challet

(10) Patent No.: US PP16,398 P3
(45) Date of Patent: Mar. 28, 2006

(54) ***CHRYSANTHEMUM* PLANT NAMED 'CHAZOU'**

(50) Latin Name: *Chrysanthemum morifolium*
Varietal Denomination: Chazou

(75) Inventor: Jean-Pierre Challet, Nuaillé (FR)

(73) Assignee: Selection New Plant Sarl, Le Luc (FR)

( * ) Notice: Subject to any disclaimer, the term of this patent is extended or adjusted under 35 U.S.C. 154(b) by 88 days.

(21) Appl. No.: 10/812,929

(22) Filed: Mar. 31, 2004

(65) Prior Publication Data

US 2005/0223448 P1 Oct. 6, 2005

(51) Int. Cl.
*A01H 5/00* (2006.01)

(52) U.S. Cl. ..... Plt./298

(58) Field of Classification Search ..... Plt./298
See application file for complete search history.

*Primary Examiner*—Kent Bell
(74) *Attorney, Agent, or Firm*—Buchanan Ingersoll PC

(57) ABSTRACT

A new and distinct *Chrysanthemum* cultivar is provided that is a whole plant mutation of the 'Chalunair' cultivar (U.S. Plant patent application Ser. No. 10/114,956, filed Apr. 4, 2002, now abandoned). The natural flowering time is mid-October. Attractive inflorescences of the spoon-type are formed that display bright red ray florets and yellow disc florets. The growth habit of the plant is rather dense, stocky, compact, and uniform. Elegant medium green foliage with flexible stems is formed. The plant displays good culture regularity and grows well in pots.

2 Drawing Sheets

Botanical/commercial classification: *Chrysanthemum morifolium*/Pot Mum.
Varietal denomination: cv. 'Chazou'.

SUMMARY OF THE INVENTION

The present invention comprises a new and distinct cultivar of *Chrysanthemum*, botanically known as *Chrysanthemum morifolium*, and hereafter is referred to by the cultivar name 'Chazou'.

The new cultivar was discovered during October 2000 at Nuaillé, France, while present in a cultivated area where plants of the 'Chalunair' cultivar (U.S. Plant patent application Ser. No. 10/114,956, filed Apr. 4, 2002, now abandoned) were being grown. The new cultivar is a naturally occurring whole plant mutation of the 'Chalunair' cultivar of unknown causation. I was initially attracted to the new cultivar primarily because of its distinctive flower coloration. Had the new cultivar not been discovered and preserved, it would have been lost to mankind.

It was found that the new *Chrysanthemum* cultivar of the present invention displays:

(a) a rather dense, stocky, compact, and uniform growth habit, (b) forms attractive spoon-type inflorescences with red ray florets and yellow disc florets, (c) forms elegant medium green foliage with flexible stems, and (d) displays good culture regularity and grows well in pots.

The new cultivar can be grown singly or in clumps in pots. It also can be grown in the landscape. The red and yellow blossoms contrast nicely with the medium green foliage. Pinching is helpful to further enhance branching and produces a large number of shoots. The natural flowering time is mid-October.

Asexual reproduction of the new cultivar by the use of cuttings as performed at Nuaillé, France, in a controlled environment has demonstrated that the characteristics of the new cultivar are firmly fixed and are retained through successive generations of asexual propagation. The new cultivar reproduces true to type from one generation to another by such asexual reproduction.

The new cultivar can be readily distinguished from the 'Chalunair' parental cultivar. More specifically, the 'Chalunair' cultivar forms red-purple inflorescences and the new cultivar forms dissimilar red ray florets.

The 'Chazou' has not been observed under all possible environmental conditions to date. Accordingly, it is possible that the phenotype may vary somewhat with variations in the environment, such as temperature, light, day length, contact with pesticides and/or subjection to grown regulation treatments.

BRIEF DESCRIPTION OF THE PHOTOGRAPH

The accompanying photographs illustrate the new 'Chazou' cultivar at an age of three months while growing in a greenhouse at Nuaillé, France.

DETAILED DESCRIPTION

Figure 1:
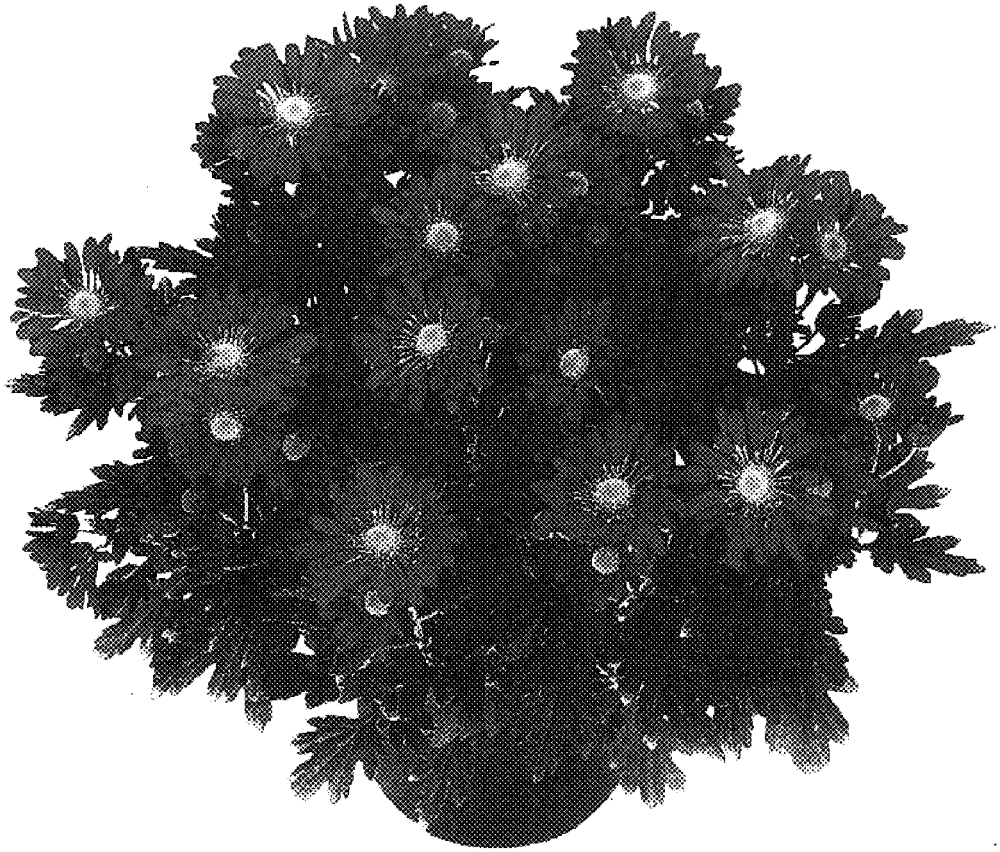
FIG. 1 shows an overall flowering plant of the new cultivar while growing in a pot. The rather dense, stocky, compact and uniform growth habit is illustrated.
Figure 2:
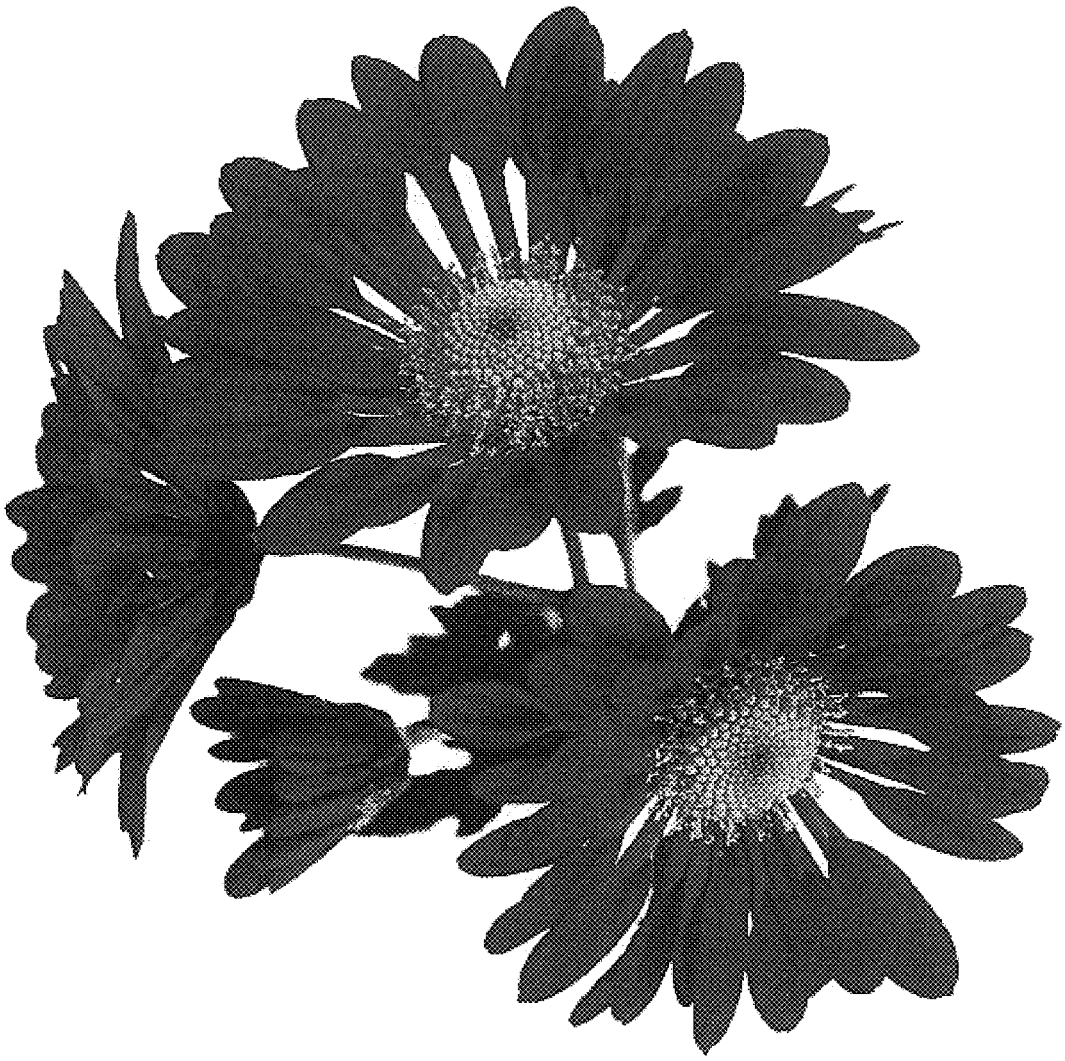
FIG. 2 shows a closer view of the attractive spoon-type inflorescences with red ray florets and yellow disc florets of the new cultivar.

The plants described were approximately three months of age and were being grown in pots in a greenhouse at Nuaillé, France. No growth regulation was used. The growing conditions approximate those commonly utilized for the commercial production of decorative pot mums. Color information is provided by reference to the R.H.S. Colour Chart of The Royal Horticultural Society, London, England.

General appearance:

Rather dense, stocky, compact, and uniform growth habit. The plant height commonly is approximately 40 to 45 cm on average and the plant width commonly is approximately 25 to 30 cm on average. The branches commonly measure approximately 35 to 40 cm in length on average, and approximately 0.7 to 1.1 cm in diameter on average. The branch coloration commonly is near Yellow-Green Group 146C. The internode length commonly is approximately 2.5 to 3.5 cm on average. The leaf apex generally is acuminate, and the leaf base in rounded and sometimes asymmetrically rounded.

Foliage:

The leaves commonly are approximately 6 to 9 cm in length on average and approximately 2.5 to 4 cm in width on average. Each leaf is medium denticulate and consists of five lobes. The leaf base commonly is rounded and the leaf apex commonly is acuminate. The leaf texture is fleshy, and the sinus between the lateral lobes is rounded and the sinus edges between lateral lobes are convergent. There commonly are approximately 26 to 30 leaves per stem. The leaf coloration is medium green (near Green Group 137A) on both surfaces. The petiole commonly is near Green Group 137A in coloration, is fleshy, is approximately 2.2 to 3.2 cm in length on average, and is approximately 0.4 to 0.7 cm in diameter on average.

Inflorescences:

Attractive red blossoms with a yellow center are formed in clusters. Commonly approximately 8 to 10 inflorescences per stem are formed on average. The buds are high-pointed and commonly possess a length of approximately 1 to 1.5 cm on average, a diameter of approximately 0.9 to 1.4 cm on average and are near Red Group 46A and 46B in coloration at the opening of the calyx. The inflorescences possess no fragrance. The disc commonly is approximately 1.5 to 1.8 cm in diameter. The disc florets are tubular, possess a slightly dentate apex, possess a pointed base, are approximately 0.6 to 0.8 cm in length on average, are approximately 0.1 to 0.3 cm in width on average, and commonly number approximately 100 to 150 on average. The disc florets initially are near Yellow-Green Group 154A in coloration, and with maturity assume a coloration of near Yellow Group 1A. The ray florets are of the spoon-type, possess a tubular base, possess a spatulate apex that is slightly dentate, possess a smooth texture, are approximately 2.5 to 3.5 cm in length on average, are approximately 0.4 to 0.7 cm in width on average, commonly number between approximately 25 to 30 on average, and during the course of opening are near Red Group 45B on the upper surface and near Red Group 46A on the under surface. Such red coloration is substantially maintained and when fully open becomes Red Group 45C on the upper surface and near Red Group 46B on the under surface. The margins of the ray florets are smooth and entire. The tubular base of the ray florets commonly measures approximately 1.3 to 2.2 cm in length on average. The spatulate apex or spoon of the ray florets commonly measures approximately 1.5 to 1.8 cm in length on average, and commonly is less than one-half the length of the tubular base. The inflorescence diameter when mature commonly ranges from approximately 5.5 to 7 cm on average. The phyllaries are extremely rudimental in character and are incapable of more precise characterization. The peduncle possesses a smooth surface texture, a length of approximately 3 to 5 cm on average, a diameter of approximately 0.4 to 0.6 cm on average, and commonly is near Green Group 137A in coloration. The receptacle possesses a high-cupola shape, a length of approximately 0.8 to 1.3 cm on average, a width of approximately 0.7 to 1.2 cm on average, and commonly is near Green Group 138A in coloration. The androecium and gynoecium reproductive parts are present among both the disc and ray florets. The reproductive organs mature first among the ray florets where pollen is well hidden, and subsequently among the disc florets beginning at the outside and progressing towards the center. However, the stigma, styles, filaments, and anthers are so small and slim that it is not possible to determine their coloration and to provide additional characterization using standard evaluation techniques. Some yellow pollen can be observed at the end of the blooming. No seeds have been observed.

Flower time:

The natural flowering time is mid-October. The duration of the blooming is approximately two weeks. The inflorescences commmonly last approximately two weeks on average on the plant and such longevity commonly is influenced by the environmental condition that are encountered. As previoulsy indicated, the ray florets of the inflorescences will retain their attractive bright red coloration.

Usage:

Pot mum. No particular susceptibility to diseases and pests has been observed during the growing of the new cultivar to date.

I claim:

1. A new and distinct cultivar of *Chrysanthemum* plant that displays:

(a) a rather dense, stocky, compact and uniform growth habit, (b) forms attractive spoon-type inflorescences with red ray florets and yellow disc florets, (c) forms elegant medium green foliage with flexible stems, and (d) displays good culture regularity and grows well in pots;

substantially as illustrated and described.

* * * * *